(12) United States Patent
Stradella

(10) Patent No.: US 7,296,712 B2
(45) Date of Patent: *Nov. 20, 2007

(54) DEVICE FOR DISTRIBUTING A FLUID OF THE MULTI-DOSE TYPE

(75) Inventor: Guiseppe Stradella, Camogli (IT)

(73) Assignee: Valois S.A.S., Le Neubourg (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/498,790

(22) Filed: Aug. 4, 2006

(65) Prior Publication Data

US 2006/0266771 A1    Nov. 30, 2006

Related U.S. Application Data

(60) Continuation of application No. 10/770,523, filed on Feb. 4, 2004, now Pat. No. 7,108,159, which is a division of application No. 10/362,477, filed as application No. PCT/FR01/02684 on Aug. 28, 2001, now Pat. No. 6,860,411.

(30) Foreign Application Priority Data

Sep. 7, 2000    (FR) .................................. 00 11429

(51) Int. Cl.
B65D 83/20 (2006.01)
B67D 5/42 (2006.01)

(52) U.S. Cl. ............... 222/162; 222/321.8; 222/381; 222/383.3; 222/402.1

(58) Field of Classification Search ............... 222/162, 222/173, 320, 321.1, 321.7, 321.8, 321.9, 222/381, 383.3, 402.1
See application file for complete search history.

(56) References Cited

U.S. PATENT DOCUMENTS

| 3,272,391 A | 9/1966 | Meshberg |
| 4,771,769 A | 9/1988 | Hegemann et al. |
| 4,826,054 A | 5/1989 | Frutin |

(Continued)

FOREIGN PATENT DOCUMENTS

JP    10-179739 A    7/1998

(Continued)

*Primary Examiner*—Joseph A. Kaufman
(74) *Attorney, Agent, or Firm*—Sughrue Mion Pllc.

(57) ABSTRACT

A fluid dispenser device a body (1), a fluid reservoir (3), a dispensing member, such as a pump or a metering valve having a piston or a valve member that is mounted to move axially, which dispensing member is fitted to the reservoir (3), and an actuating element (5) mounted to move between a rest position and an actuating position, for actuating the dispensing member and thus for selectively dispensing the fluid contained in the reservoir (3), fluid dispenser device being characterized in that the direction in which actuating element (5) moves is different from, and in particular perpendicular to, the axial direction in which the piston or the valve member of the dispensing member moves, the actuating element (5) having an end portion provided with the cam surface (6) which co-operates with the reservoir (3) or a fixing ring (8) adapted to fix the dispensing member to the reservoir (3) so that the actuating element (5) being moved substantially radially into its actuating position causes the reservoir (3) to be moved axially relative to the piston or to the valve member of the dispensing member so as to dispense a dose of fluid.

20 Claims, 2 Drawing Sheets

U.S. PATENT DOCUMENTS

| | | |
|---|---|---|
| 5,040,705 A | 8/1991 | Snell |
| 5,615,577 A | 4/1997 | Chen |
| 5,899,365 A | 5/1999 | Eichler et al. |
| 6,095,379 A | 8/2000 | Martinez et al. |
| 6,340,103 B1 | 1/2002 | Scheindel et al. |
| 6,419,124 B1 | 7/2002 | Hennemann et al. |
| 6,454,153 B2 | 9/2002 | Bettinger et al. |
| 6,494,349 B1 | 12/2002 | Thompson et al. |
| 6,860,411 B2 * | 3/2005 | Stradella ............ 222/321.8 |
| 7,108,159 B2 * | 9/2006 | Stradella ............ 222/162 |

FOREIGN PATENT DOCUMENTS

WO      WO98/12511 A2     3/1998

* cited by examiner

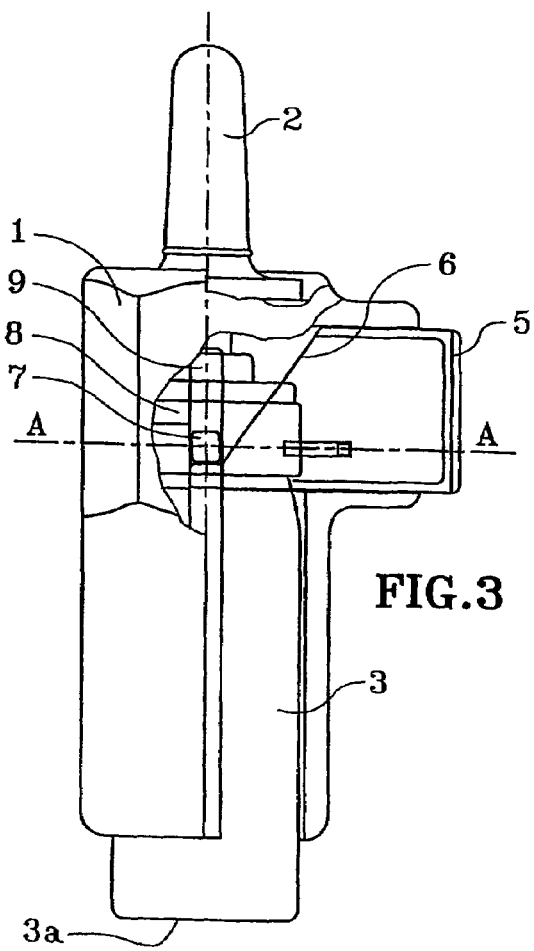
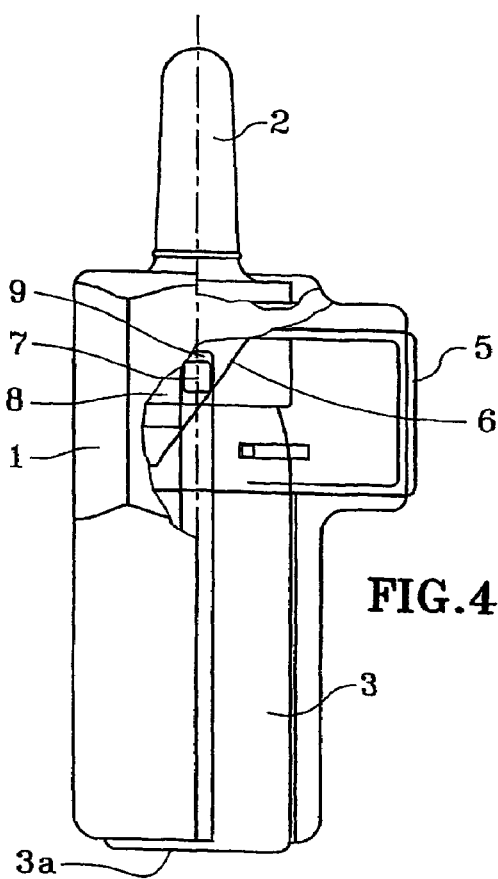
FIG.3
FIG.4
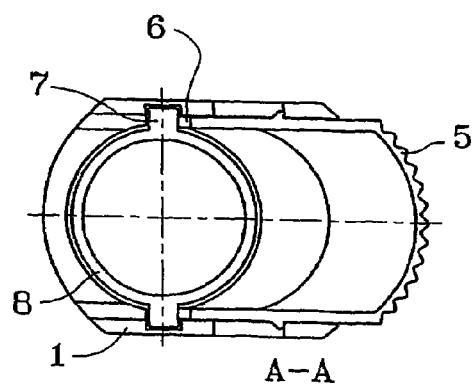
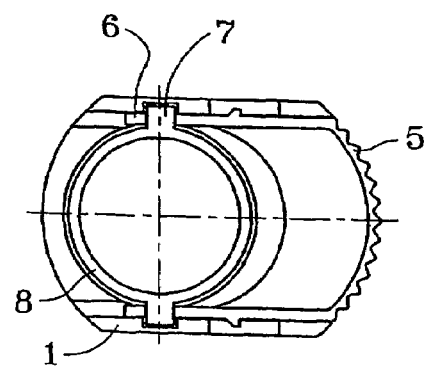
FIG.5
FIG.6

DEVICE FOR DISTRIBUTING A FLUID OF THE MULTI-DOSE TYPE

CROSS-REFERENCE TO RELATED APPLICATION

This is a continuation of application Ser. No. 10/770,523 filed Feb. 4, 2004, now U.S. Pat. No. 7,108,159, which is a Divisional of application Ser. No. 10/326,477, filed Feb. 24, 2003, now U.S. Pat. No. 6,860,411, which is a National Stage Application filed under §371 of PCT Application No. PCT/FR01/02684, filed Aug. 28, 2001. The entire disclosures of the above prior applications are all hereby incorporated by reference.

FIELD OF INVENTION

The present invention relates to a fluid dispenser device, and more particularly to a fluid spray device of the multi-dose type having a lateral actuating system.

In the field of multi-dose spray devices, several systems for laterally actuating the pump of the device have been developed recently.

BACKGROUND

Such a system is generally constituted by a body containing the entire spray device and provided with a pivotally mounted lever system acting against the end-wall of the fluid reservoir and pushing it axially, during actuation, towards the dispensing head so as reproduce the movement of the hand during standard axial actuation.

Such systems suffer from numerous problems. In particular, they do not make it possible for a standard assembly method to be implemented by the manufacturer of the fluid to be dispensed, which is generally a pharmaceutical, because it is then not possible merely to insert the unit formed by the reservoir and by the pump into the dispensing head, as is usual in devices that are actuated by hand. In addition, such systems make lateral actuation essential, even though the user might, for various reasons, such as dexterity problems, a habit difficult to change, etc. sometimes prefer to actuate the device in the conventional manner, i.e. by pressing by hand on the end-wall of the reservoir. In addition, all of the existing lateral actuating systems do not solve the problem which is typical with most spray pumps and which relates to the dose-metering accuracy and the spray quality being dependent on the speed and the force with which the user actuates the device. Thus, partial actuation can result in a partial dose being dispensed or in the spray quality being degraded.

SUMMARY OF THE INVENTION

An object of the present invention is to provide a fluid dispenser device that does not reproduce the above-mentioned drawbacks.

In particular, an object of the present invention is to provide a fluid dispenser device that is simple and inexpensive to manufacture and to assemble.

Another object of the present invention is to provide a fluid dispenser device that guarantees excellent spray quality and delivery of a full dose of fluid each time it is actuated, independently of the resistance of the pump and/or of the quantity of fluid and/or of the actuating force exerted by the user on the actuating element.

Another object of the invention is to provide a fluid dispenser device that can be actuated by a lateral actuating system or by a standard actuating system, i.e. by pushing axially on the end-wall of the reservoir towards the dispensing orifice.

Another object of the present invention is also to provide a laterally-actuated fluid dispenser device in which assembly of the device by the fluid manufacturer is not modified by the presence of the lateral actuating system, i.e., after the reservoir has been filled, the unit formed by the reservoir and by the dispensing member is merely fixed inside the remainder of the device.

To these ends, the present invention provides a fluid dispenser device comprising a body, a fluid reservoir, a dispensing member, such as a pump or a metering valve having a piston or a valve member that is mounted to move axially, which dispensing member is fitted to the reservoir, and an actuating element mounted to move between a rest position and an actuating position, for actuating the dispensing member and thus for selectively dispensing the fluid contained in the reservoir, said fluid dispenser device being characterized in that the direction in which said actuating element moves is different from, and in particular perpendicular to, the axial direction in which the piston or the valve member of the dispensing member moves.

The actuating element having an end portion provided with a cam surface which co-operates with the reservoir or a fixing ring adapted to fix the dispensing member to the reservoir so that the actuating element being moved substantially radially into its actuating position causes the reservoir to be moved axially relative to the piston or to the valve member of the dispensing member so as to dispense a dose of fluid.

Advantageously, the actuating element is provided with return means for returning it from its actuating position to its rest position after each occasion on which the device is actuated.

Advantageously, the reservoir and said dispensing member form a first unit, said body and said actuating member form a first unit, said body and said actuating element forming a second unit, said first unit being fixed, in particular by snap-fastening, into said second unit.

Advantageously, after fixing of said first unit in said second unit, the end-wall of the reservoir remains accessible for being actuated by hand by pushing axially on said end-wall of the reservoir.

Advantageously, the reservoir and said dispensing member form a first unit and said body, said actuating element and said force-regulating means form a second unit, said first unit being fixed, in particular by snap-fastening, into said second unit such that the end-wall of the reservoir remains accessible for being actuated by hand by pushing axially on said end-wall of the reservoir.

In a first variant embodiment of the invention, said dispensing member is a pump including a piston.

In a second variant embodiment of the invention, said dispensing member is a metering valve including a valve member.

BRIEF DESCRIPTION OF FIGURES

Other characteristics and advantages of the present invention will appear more clearly on reading the following detailed description of two embodiments of the invention, given with reference to the accompanying drawings which are given by way of non-limiting example, and in which:

FIG. 3 is a partially cutaway section view of a second embodiment of the invention, in the rest position;

FIG. 4 is a view similar to the FIG. 3 view, in the actuating position;

FIG. 5 is a diagrammatic horizontal section view, seen looking from above, of the device shown in FIG. 3, in the rest position; and FIG. 6 is a view similar to the FIG. 5 view, in the actuating position.

BRIEF DESCRIPTION OF THE INVENTION

Figure 1:
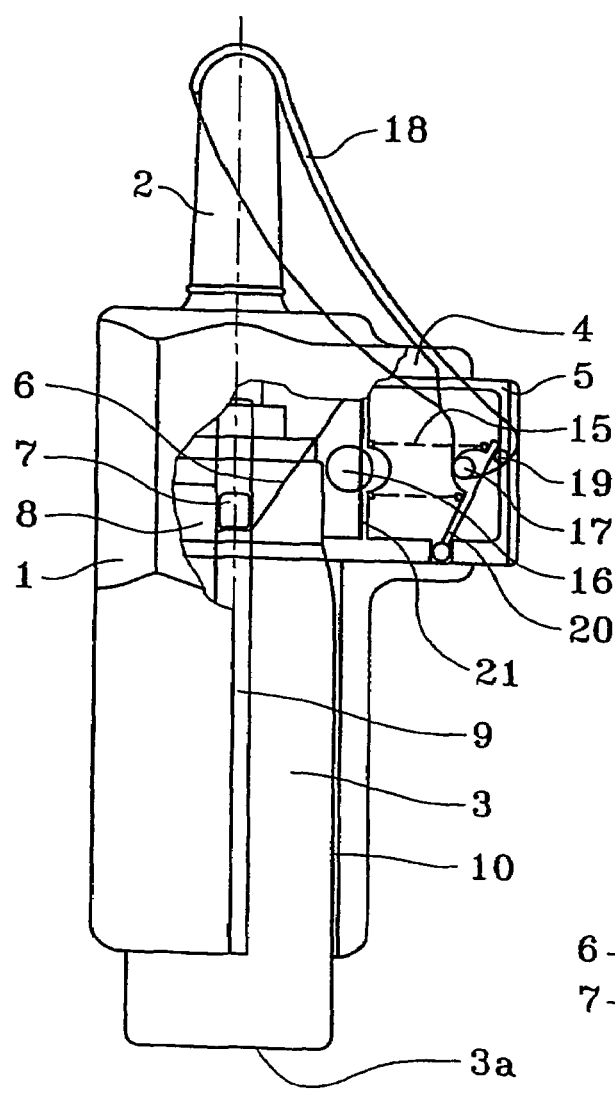
FIG. 1 is a partially-cutaway diagrammatic section view of a first embodiment of a fluid dispenser device of the present invention, in the rest position.

With reference to the drawings, the device of the invention includes a reservoir 3 to which a dispensing member (not shown) such as a metering valve or a pump is fixed. The examples shown in the drawings relate to a device having a pump which operates with a piston moving inside a metering chamber to deliver a metered quantity or "dose" of fluid, as is well known, but the invention is also applicable to inhalers of the metered dose inhaler (MIDI) type having a metering valve and generally used upside down. In which case, it is the valve member of the valve that moves relative to the reservoir to deliver the dose.

The dispensing member, referred to below by the term "pump", is fitted to the reservoir 3 preferably by means of a fixing ring 8. The unit formed by the reservoir and the pump is inserted into a body 1 which incorporates a nasal applicator 2 provided with a dispensing orifice.

Although it is shown in the examples in the form of a nasal-type dispenser, the invention is also applicable to other types of dispenser devices, e.g. inhalers of the oral type or the like.

In the invention, the device includes an actuating element 5 which is adapted to actuate the pump to deliver a dose of fluid. The actuating element 5 is disposed on one side, and it is mounted to move in a direction that is different from and in particularly substantially perpendicular to the axial direction in which the piston moves in the pump. Thus, the actuating element 5 has an end portion provided with a cam surface 6 which cooperates with one or more projections 7 provided on the reservoir 3 or on the fixing ring 8. In the examples shown, the radial projections 7 are implemented in the form of pairs which are integral with the fixing ring 8. The cam surface of the actuating element 5 is advantageously made in the form of a slope 6 which co-operates with said projections 7 to transform a substantially radial movement of the actuating element 5 into an axial movement of the piston of the pump so as to dispense a dose of fluid. When the actuating element 5 ceases to be pressed, said actuating element is returned to its rest position by the return spring of the piston.

The device may include force-regulating means which are adapted to predetermine the force exerted by the actuating element 5 on said projections 7, independently of the resistance of the pump and/or of the quantity of liquid in the reservoir and/or of the actuating force exerted by the user on the actuating element 5.

Figure 2:
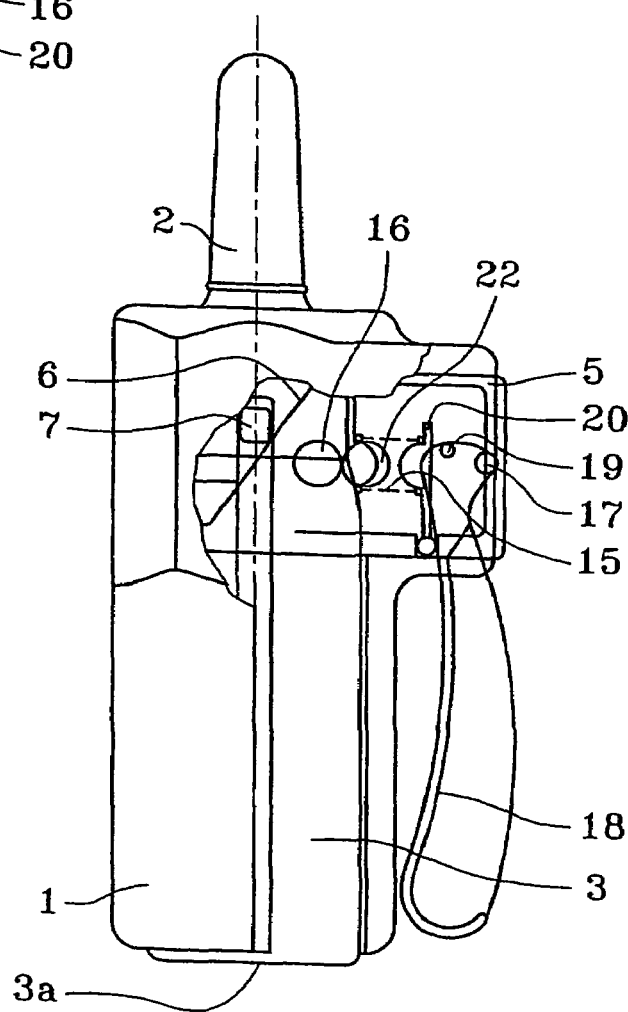
FIG. 2 is a view similar to the FIG. 1 view, in the actuating position.

In a first embodiment shown in FIGS. 1 and 2, the force-regulating means comprise resilient means such as a spring 15 which co-operates with the actuating element 5 to urge it towards its actuating position when the spring is compressed. The force-regulating means further include trigger means 16 that are preferably implemented in the form of one or more side buttons. The buttons 16 retain the actuating element in the rest position (shown in FIG. 5) against the force exerted by the spring 15, until the user presses on the buttons 16 to release the locking of the actuating element 5, thereby enabling it to move into its actuating position under the effect of the resilient force of the spring 15, and thus to move the reservoir 3 relative to the piston of the pump to deliver a dose. It is thus the characteristics of the spring 15 that determine the force exerted by the actuating element on the pump, and therefore the actuating force on the pump is independent of the force exerted by the user on the actuating element 5. Advantageously, the spring 15 co-operates with a loading element 18 which is moved by hand to compress said spring 15. As shown in the drawings, the loading element 18 may be implemented in the form of a cover which, in the rest position, closes off the dispensing orifice of the device, and which is mounted on the body 1 to pivot about a pivot pin 17, said cover 18 further being provided with a transverse control peg 19 which co-operates with a lever 20. When the cover 18 is opened, as shown in FIG. 2, the peg 19 acts against the lever 20 which compresses the spring 15 against an internal wall 21 formed inside the actuating element 5. In this position, the actuating element 5 is held in its rest position by the pair of buttons 16. Preferably, the buttons 16 are formed on flexible arms (not shown) which are secured to or integral with the actuating element 5, and which, when the actuating element 5 is in the rest position, are urged resiliently into holes 22 in the body 1. When the user presses laterally on the buttons 16, which are formed in suitable manner, they are disengaged from the retaining holes 22, thereby releasing the actuating element 5 which, under drive from the spring 15, slides inside the sleeve 4 of the body 1 to actuate the pump. It should be noted that, while the actuating element is being displaced, the pivot pin 17 via which the cover 18 pivots on the body 1 does not prevent the actuating element 5 from moving because said cover is provided with two suitable slots (not shown) in its sides so as to prevent any interference with the pegs forming the pivot pin 17.

Optionally, the actuating element may further be provided with resilient return means that return the actuating element to its rest position after each occasion on which the device is actuated. Generally, however, the force of the return spring of the piston of the pump suffices to return the actuating element 5 to its rest position, by means of the projections 7 pushing on the sloping surface 6. Preferably, while the actuating element 5 is returning to its rest position 16, the buttons 16 return automatically into the holes 22 in the body, and the device is ready to be used again.

If desired, said return means for returning the actuating element 5 to its rest position can be actuated only when the cover 18 is returned to its closure position in which it closes off the dispensing orifice as shown in FIG. 1. In which case, it is guaranteed that the user must close the cover, and thus protect the dispensing orifice of the device, after each occasion on which it is used.

In FIGS. 3 to 6, a second embodiment is shown that differs from the embodiment shown in FIGS. 1 and 2 in that the device does not have the pre-compressible resilient means for exerting a force on the actuating element 5 during actuation of the device. In the example shown in FIGS. 3 to 6, the force exerted by the user on the lateral actuating element 5 is directly transformed into a force for axially moving the piston of the pump by the slope 6 forming the cam surface and co-operating with the peg 7 integral with the fixing ring 8. In this embodiment, the force-regulating means may be implemented in the form of a varying gradient of said sloping surface 6. During the actuating stroke, pumps generally change their resistance, and therefore the force required for actuation. Such increases in resistance during the stroke take place sometimes constantly, and sometimes very quickly. An appropriate variation in the inclination of the cam surface 6 can fully compensate for such increases in resistance, thereby enabling actuation be safe, with resulting accurate metering and excellent spraying, while exerting a constant force on the actuating element 5.

The device of the invention thus offers the following advantages:

- actuation is lateral, and is therefore often easier and more comfortable for the user;
- the lateral actuating system unit is assembled onto the body 1, in the vicinity of the nasal applicator 2 of the device so that the end-wall of the reservoir 3 may be freely accessible; this makes it possible for standard conventional actuation to be performed by axially pressing on the bottom of the reservoir if necessary; this can be decisive in the event of an attack, e.g. an asthma attack, when the user, in a panic, attempts to actuate the device in the manner to which the user has been accustomed for many years, i.e. by pushing on the end-wall of the reservoir;
- assembly by the manufacturer of the fluid to be dispensed is not modified by the presence of a lateral actuating system, it being possible for the unit formed by the reservoir and by the pump to be mounted simply in the body, as in existing devices; the lateral actuation in no way modifies assembly of the device, which is a considerable advantage; and
- since the lateral actuating system is independent of the size of the reservoir, the present invention makes it possible to adapt reservoirs of various dimensions to fit inside the same body 1 without modifying the production line on which the device is manufactured.

Although shown in relation to a pump having a piston and operating in the upright position in the drawings, the invention, as specified above, is also applicable to metering valves for inhalers of the MIDI type. In addition, the invention is not limited to the embodiments shown in the figures, and modifications may be considered within the ambit of the invention as defined by the accompanying claims.

The invention claimed is:

1. A fluid dispenser device comprising a body (1), a fluid reservoir (3), a dispensing member having a piston or a valve member that is mounted to move axially, and an actuating element (5) mounted to move between a rest position and an actuating position, for actuating the dispensing member and thus for selectively dispensing the fluid contained in the reservoir (3), said fluid dispenser device being characterized in that the direction in which said actuating element (5) moves is different from the axial direction in which the piston or the valve member of the dispensing member moves, a cam surface provided on a radially inner edge of the actuating element (6) which abuts an abutting member which is movable and rides on the cam surface, the abutting member being coupled to the reservoir (3) or a fixing ring (8) adapted to fix the dispensing member to the reservoir (3), so that the actuating element (5) being moved substantially radially into its actuating position causes the abutting member to move along the cam surface and the reservoir (3) to be moved axially relative to the piston or to the valve member of the dispensing member so as to dispense a dose of fluid.

2. A device according to claim 1, in which said cam surface comprises a sloping surface (6) and the abutting member comprises at least one projection (7) integral with the reservoir (3) or with the fixing ring (8).

3. A device according to claim 1, in which said actuating element (5) is provided with return means for returning it from its actuating position to its rest position after each occasion on which the device is actuated.

4. A device according to claim 3, in which the reservoir (3) and said dispensing member form a first unit, said body (1) and said actuating element (5) forming a second unit, said first unit being fixed into said second unit.

5. A device according to claim 4, in which, after fixing of said first unit in said second unit, the end-wall (3*a*) of the reservoir (3) remains accessible for being actuated by hand by pushing axially on said end-wall of the reservoir.

6. A device according to claim 1, in which said dispensing member is a pump including a piston.

7. A device according to claim 1, in which said dispensing member is a metering valve including a valve member.

8. A device according to claim 1, wherein the dispensing member is at least one of a pump or a metering valve.

9. A device according to claim 1, wherein the actuating element moves perpendicular to the axial direction in which the piston or the valve member of the dispensing member moves.

10. A device according to claim 4, wherein the first unit is fixed into the second unit by snap-fastening.

11. A fluid dispenser comprising:
- a body;
- a fluid reservoir;
- a dispensing member movable in an axial direction; and
- an actuating element which is moved between a rest position and an actuating position to actuate the dispensing member;
- wherein, the direction in which the actuating element moves is different from the axial direction in which the dispensing member moves;
- wherein the actuating element comprises a cam surface located on a radially inner edge of the actuating element; and
- wherein the cam surface abuts an abutting member and the abutting member moves in response to actuation of the actuating element.

12. The fluid dispenser of claim 11, wherein the abutting member is coupled to at least one of the fluid reservoir and a fixing ring which fixes the dispensing member to the reservoir.

13. The fluid dispenser of claim 12, wherein the abutting member is movable along the cam surface, so that when the actuating element is actuated, the abutting member moves along the cam surface and the reservoir is moved axially relative to the dispensing member so as to dispense a dose of fluid.

14. The fluid dispenser of claim 11, wherein the abutting member moves relative to the body.

15. The fluid dispenser of claim 13, wherein the cam surface is a sloped surface.

16. The fluid dispenser of claim 14, wherein the cam surface has a varying gradient.

17. The fluid dispenser of claim 13, wherein the actuating element moves perpendicular to the axial direction in which the dispensing member moves.

18. The fluid dispenser of claim 13, wherein the dispensing member comprises a piston or a valve member and the abutting member comprises a projection.

19. The fluid dispenser of claim 13, wherein pressing a surface of the reservoir also actuates the fluid dispenser to dispense a dose of fluid.

20. The fluid dispenser of claim 11, wherein the abutting member remains axially fixed relative to the reservoir during actuation of the actuating element.

* * * * *